United States Patent
Zachery

(10) Patent No.: US 6,224,582 B1
(45) Date of Patent: May 1, 2001

(54) DIAPER INSERT FOR ADULT INCONTINENT PATIENTS

(76) Inventor: Michael K. Zachery, 3014 Granada, Mesquite, TX (US) 75181

( * ) Notice: Subject to any disclaimer, the term of this patent is extended or adjusted under 35 U.S.C. 154(b) by 0 days.

(21) Appl. No.: 09/484,327

(22) Filed: Jan. 18, 2000

(51) Int. Cl.[7] ................................................. A61F 13/15
(52) U.S. Cl. ........................... 604/385.14; 604/385.3; 604/385.27; 604/385.25
(58) Field of Search ........................ 604/385.14, 385.25, 604/385.3, 385.27

(56) References Cited

U.S. PATENT DOCUMENTS

| | | | | |
|---|---|---|---|---|
| 3,882,871 | * | 5/1975 | Taniguchi | 128/287 |
| 4,834,737 | * | 5/1989 | Khan | 604/385.2 |
| 5,005,525 | * | 4/1991 | Stanton | 119/95 |
| 5,207,665 | * | 5/1993 | Davis et al. | 604/399 |
| 5,217,447 | * | 6/1993 | Gagnon | 604/397 |
| 5,261,901 | * | 11/1993 | Guay | 604/391 |
| 5,554,145 | * | 9/1996 | Roe et al. | 604/385.2 |
| 5,601,547 | * | 2/1997 | Kato et al. | 604/385.2 |
| 5,607,416 | * | 3/1997 | Yamamoto et al. | 604/397 |
| 5,669,902 | * | 9/1997 | Sivilich | 604/396 |
| 5,876,391 | * | 3/1999 | Roe et al. | 604/385.2 |
| 5,904,673 | * | 5/1999 | Roe et al. | 604/385.2 |
| 5,947,948 | * | 9/1999 | Roe et al. | 604/385.2 |

* cited by examiner

*Primary Examiner*—John G. Weiss
*Assistant Examiner*—Paul Shanoski
(74) *Attorney, Agent, or Firm*—Crutsinger & Booth; James O. Dixon

(57) ABSTRACT

A disposable insert for use with an adult diaper, said insert having a webbed "T" configuration and a plurality of absorbent pads or batts, one of which is positioned at the lower end of the "T" configuration such that when the insert is placed on the patient wide portion across the patient's abdomen and narrow portion positioned through the patient's crotch, fluid tending to puddle is absorbed without leakage. The insert may be applied to the patient with very little, if any, lifting of the patient required.

7 Claims, 2 Drawing Sheets

DIAPER INSERT FOR ADULT INCONTINENT PATIENTS

TECHNICAL FIELD

The present invention relates to adult sanitary garments such as diapers for bed-ridden and weak or paralyzed patients, especially for larger patients.

BACKGROUND OF INVENTION

Sanitary garments in the nature of diapers are often used for patients who are bed-ridden because of weakness or paralysis and for any of several reasons may not be able to use a bed pan or other facility to attend to their elimination needs.

The attendant care giver may find it difficult because of the patient's size or inability to help to change or replace a diaper or sanitary garment of the usual size because in most instances the patient's body between waist and knees must be raised at least to some extent from the bed in order to remove and replace the garment. This is because the garment, to stay in place and properly perform its function, must fit the patient's body snugly and around his thighs and up his back and front around his abdomen in an area just a bit below the waist.

The present invention allows sanitary care for a patient without a full change of diaper garment as frequently as previously required.

SUMMARY OF INVENTION

The present invention comprises an insert device for an adult diaper in which the materials of construction are the same or quite similar to those used in currently available large diapers. The insert of the present invention is, however, shaped and formed so that when used in conjunction with a full diaper, the insert may be strategically placed between the patient and the diaper so as to absorb fluid waste and moisture without spill over into the main diaper. Because the insert of the present invention is held in position by a diaper of the usual type worn in the ordinary manner, it need not extend so far up the patient's back that lifting is required to properly position the insert. Thus, the change of a soiled insert does not entail the lifting as would be required to change a full diaper.

BRIEF DESCRIPTION OF THE DRAWINGS

Annexed hereto for a better and more complete understanding of the invention as set forth in the following detailed description of the preferred embodiment of the invention are drawings in which.

DETAILED DESCRIPTION OF THE INVENTION

Figure 1:
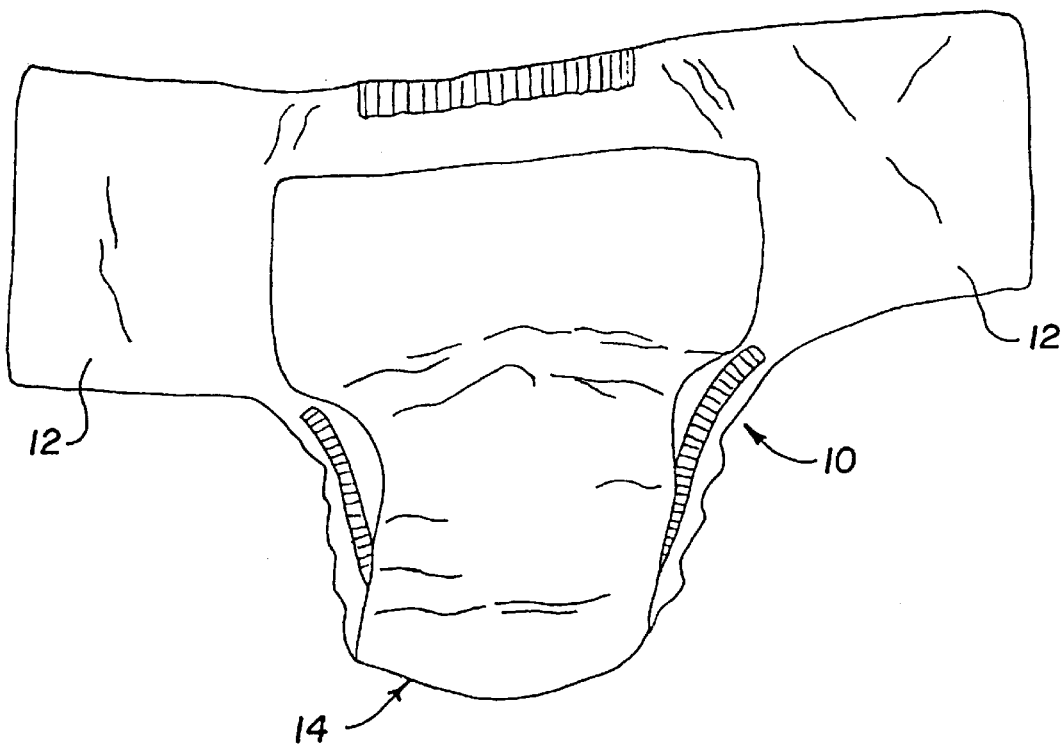
FIG. 1 is an inside or front view looking toward the inner or absorbent surface of the insert of the present invention.
Figure 2:
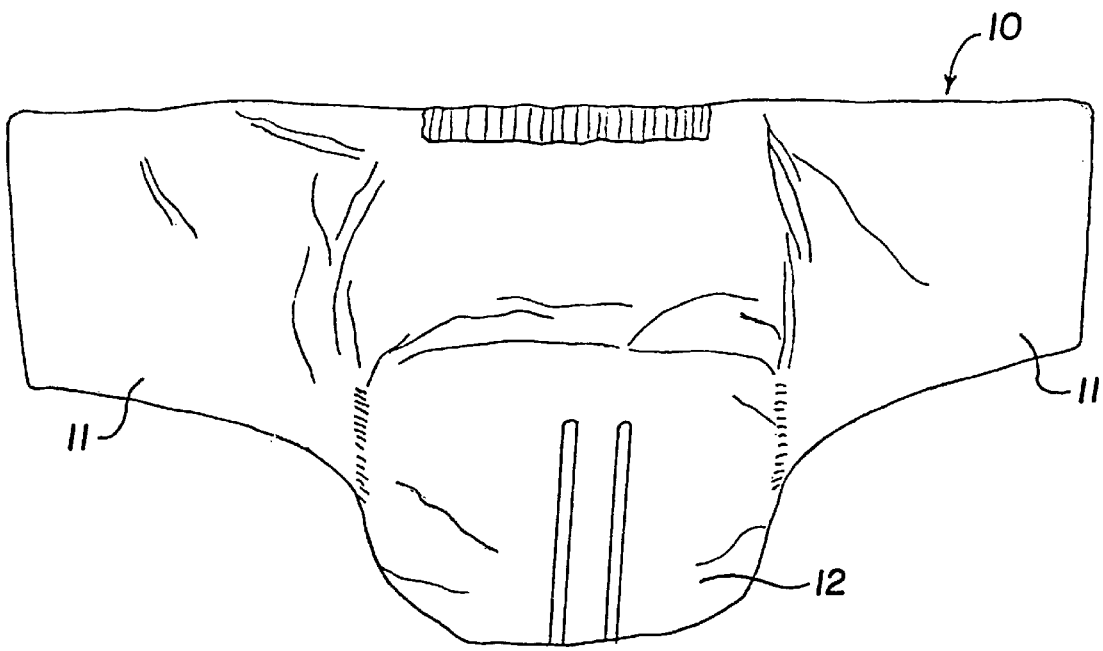
FIG. 2 is an outside or back view looking toward the impervious outside of the insert of the present invention.

Referring now to FIGS. 1 and 2, the diaper insert of the present invention is shown from an inside view, FIG. 1, and from an outside view, FIG. 2. The insert 10 is multi-layered and of a generally "webbed T" configuration. By "webbed T" as used herein is meant a "T" having a web or fillet extending from each end of the cross member to the lower end of the vertical member of the "T."

The exterior or backing sheet 11 is of a light fluid-impervious plastic material and may be of any of the types used in disposable diapers, infants and adults, currently available from any of the several manufacturers of such items.

An interior layer or liner sheet 12 of essentially the same configuration as the outer layer 12 is a very thin soft matting layer of soft fiber material such as a cotton designed to provide a comfortable shield for the skin of the wearer from potentially irritating or perhaps uncomfortable contact with the outer layer.

A third layer 13 (see FIG. 3) is a batt of soft highly-absorbent fiber such as cotton or any of the other suitable materials currently used in commercially available disposable diapers as the main absorbent layer. Layer batt 13 is sandwiched between backing sheet 11 and liner sheet 12. Batt 13 is of an oblong configuration as shown, somewhat narrower and shorter than sheet 11 and sheet 12. For reasons to be explained later, a small additional layer 20 being a batt of the same or similar highly absorbent material as sheet 13 is placed at the region 14 at the narrow lower end of sheet 13 to provide a double thickness of absorbent material.

One additional member 15 being a batt of highly-absorbent fiber material such as cotton having a generally oblong or keystone shape is interposed between sheet 12 (shown cut away in FIG. 3) and batt 13. Layer 15 acts as a reservoir for fluid accumulation.

It is to be understood that batts 14 and 15 may be positioned on the other side of batt 13 without serious effect on the action of the insert of this invention.

Figure 3:
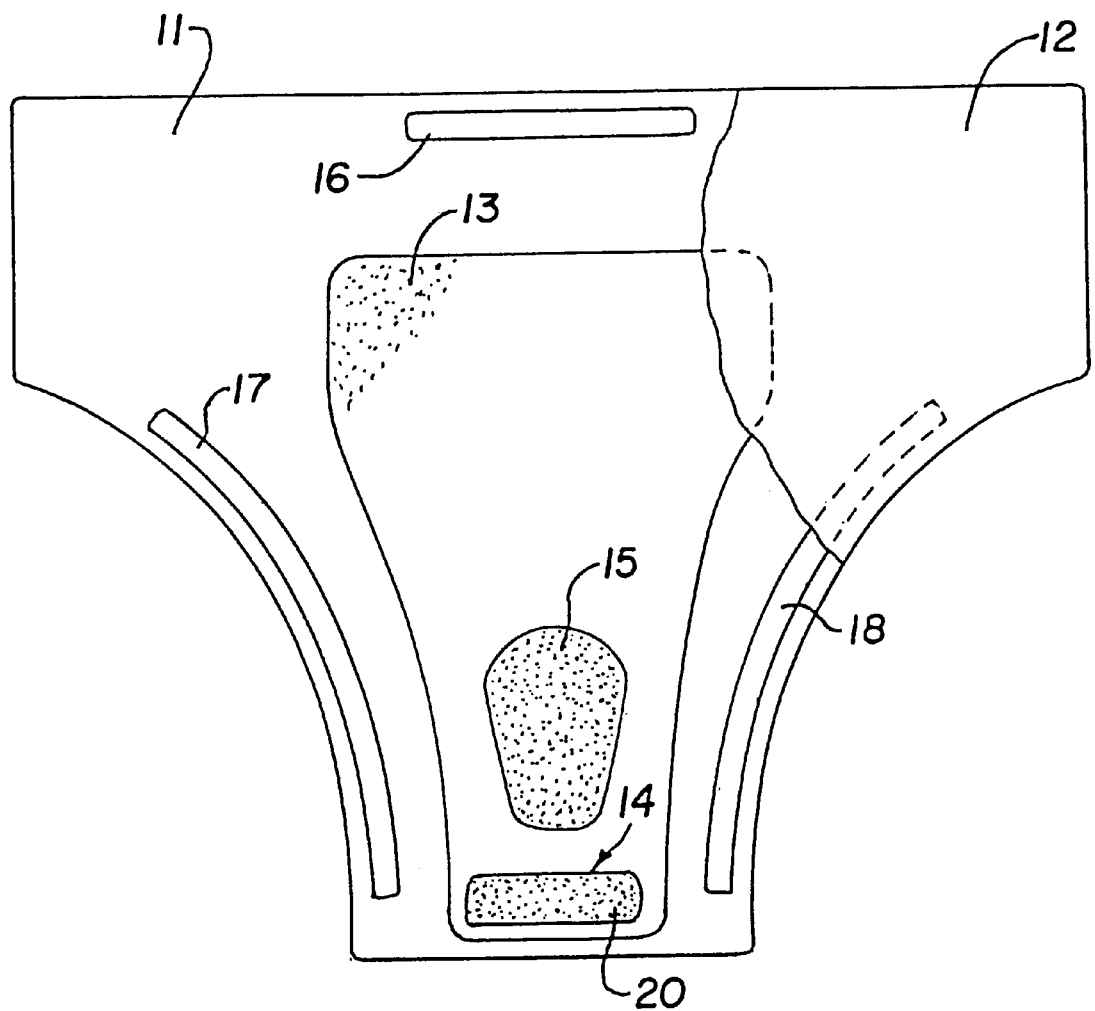
FIG. 3 is a plan view of an assembly stack of the various layers of materials of the insert of the present invention illustrating their relative size and configuration.

The general shapes and relative positions of the various layers of the diaper insert 11 of the present invention are shown in FIG. 3 depicting sheet 11 and batts 13, 15 and 20 positioned for assembly.

To complete the diaper insert of the present invention, elastic strips 16 for the waist and 17 and 18 for the legs are positioned as shown in FIG. 3 between the outer sheet 11 and the liner sheet 12.

The various layers and strips of the insert of the present invention are adhered together in their relative positions as shown by the usual means and techniques well-known in the diaper industry.

By way of example only, the proportional sizes of the various parts of an adult-sized diaper insert as described herein may be as follows. The top or long side of exterior sheet may be from about 30 inches to about 45 inches and the shorter bottom side from about 13 inches to about 16 inches; the top to bottom length may be from about 20 inches to about 30 inches, and the straight edges on the sides of the "T" crossbar may be about 9 inches long.

The waist elastic 16 may be about 16 inches extended length and the leg elastics 17 and 18 about 17 inches extended length. Batt 13 should be about 12 to 16 inches wide at the top and about 6 inches to about 9 inches or more wide at the bottom; its overall length should be from about 16 inches to about 19 inches with batt 20 being about the width of the bottom end of batt 13 and about 2 inches or more in length to provide the double thickness as previously noted. Reservoir batt 15 may be in the range of about 5 inches wide by about 5 or more inches long. Batts 13, 15 and 20 may be about three-eighths inch or more thick.

Of course the actual shapes and sizes of the various batts and sheets are not critical and may be varied as desired or required.

The dimensions given above are for adult wear of from small to about medium size and may be adjusted for larger or smaller persons.

As previously noted, the insert of the present invention makes it unnecessary to lift the lower body of a bed-ridden user fully off the bed surface (as one would in changing a regular diaper) to change the insert. For example, to change the regular adult diaper, the wearer's legs, hips and buttocks must be lifted clear of the bed sufficiently that the upper edge of the regular adult diaper maybe positioned at about the "small" of the back or about naval height. The insert of the present invention, however, is placed within the regular diaper with its upper wide region across the patient's abdomen and the narrow portion tucked between the legs and extending through the crotch area to just below the buttocks. Thus, application of the insert requires much less lifting of the patient than would be required in changing a full diaper.

For use of the insert of the present invention, the patient or user is positioned on his/her back with a clean adult diaper of the usual type placed under the hips and back in an open position ready to be closed, i.e., ready to be fastened around the patient's abdomen and legs. The insert of the present invention is as described above, placed absorbent side against the patient, the wide end across the patient's stomach and the narrow end extended down between the legs. The narrow end is tucked between the patient's legs and back up toward the folds at the beginning of the buttocks cheeks to the extent possible with knees up but without lifting hips off the bed. The wide end is smoothed across the patient's abdomen with the flap areas 19 down along the patient's sides at the hips. The lower portions are then adjusted so the elastics 17 and 18 pull the insert snugly around the legs.

The regular diaper is then closed and fastened in the usual way.

With the insert positioned described fluid emanating from the patient will be absorbed by the batts 13, 15 and 20, the absorptive capacity of these elements being essentially the same as that of a regular adult diaper. The waste fluids are retained sufficiently in the insert and held away from the regular diapers on the patient because of the imperviousness of the sheet 11 and the constrictive action of the leg elastics around the patient's legs. When the insert of the present invention is properly placed, layer 20 is effective to prevent leakage caused by "puddling" of liquid in that lowermost area due to gravity.

The tendency of fluids to "puddle" and then overflow down into the insert due to gravitational forces is greatly reduced by the presence of the doubled thickness region 14 of the absorbent layers 13 and 20.

It has been found that use of the inserts of the present invention make it unnecessary to change the regular full size diaper of a patient usually through three or more insert changes.

Thus, there has been disclosed an adult sanitary item in the form of an adult diaper insert which may inspire many changes and modifications still within the spirit and the scope of the invention, which is therefore to be limited only as set forth in the following claims.

What is claimed is:

1. A disposable insert for placement in an adult incontinent garment comprising:

a thin liquid impervious outer backing sheet of a webbed "T" configuration;

a thin liquid pervious soft inner lining sheet of essentially the same configuration as said backing sheet and adhered to said backing sheet at least along their peripheral edges;

a plurality of liquid absorbent batts positioned between said backing sheet and said lining sheet;

a first of said plurality of batts forming a first absorbent layer extending in length from near the bottom edges of said backing and said lining sheets to between about one-half to about three-quarters the distance to the upper edges of said backing and said lining sheets, the width of said first batt at its bottom being slightly less than the bottom edge widths of said backing and said lining sheets and being wider near its top edge up to about one-third the greatest width of said backing and said lining sheets;

a second of said plurality of batts lying against and across said first batt from about the bottom edge of said first batt upward for a distance of from about one and one-half inches to about two and one-half inches;

a third of said plurality of batts being generally oblong in shape and wider in its upper areas than at its bottom end and being lesser in length and in width than said first batt, said third batt being positioned against said first batt above said second batt and generally centered between the side edges of said first batt.

2. The insert as defined in claim 1 wherein said plurality of batts and said backing and lining sheets are adhered together sufficiently to retain their positional relationships.

3. The insert as defined in claim 1 further including an elastic member along and near the upper edges of said backing and said lining sheets and an elastic member along and near each of the side edges of the web of the "T" configuration of said sheets.

4. The insert as defined in claim 3 wherein each of said elastic members is sandwiched between said backing and said lining sheets.

5. The insert as defined in claim 1 wherein said backing and lining sheets are from about twenty-eight to about thirty inches in width at their upper ends and from about twenty to about twenty-four inches in length and from about eight to about nine inches in width at their lower ends.

6. The insert as defined in claim 3 wherein said backing and lining sheets are from about twenty-eight to about thirty inches in width at their upper ends and from about twenty to about twenty-four inches in length and from about eight to about nine inches in width at their lower ends.

7. A disposable insert for placement in an adult incontinent garment comprising:

a thin liquid impervious outer backing sheet of a webbed "T" configuration;

a soft thin liquid pervious inner lining sheet of essentially the same configuration as said backing sheet and adhered to said backing sheet at least along their peripheral edges;

an elastic member along and near the upper edges of said backing and said lining sheets and an elastic member along and near each of the side edges of the web of said sheets "T" configuration, each of said elastic members being sandwiched between said backing and said lining sheets;

a plurality of liquid absorbent batts positioned between said backing sheet and said to lining sheet;

a first of said plurality of batts forming a first absorbent layer extending in length from near the bottom edges of said backing and lining sheets to between about one-half to about three-quarters the distance to the upper edges of said backing and said lining sheets, the width of said first batt at its bottom being slightly less than the bottom edge widths of said backing and said lining sheets and being wider near its top up to about one-third the greatest width of said backing and said lining sheets;

a second of said plurality of batts lying against and across said first batt from about the bottom edge of said first batt upward for a distance of from about one and one-half to about two and one-half inches;

a third of said plurality of batts being generally oblong in shape and wider in its upper areas than at its bottom and lesser in length and width than said first batt and being positioned against said first batt above said second batt and generally centered between the side edges of said first batt;

said plurality of batts and said backing and said lining sheets being adhered together sufficiently to retain their positional relationships.

\* \* \* \* \*

UNITED STATES PATENT AND TRADEMARK OFFICE
CERTIFICATE OF CORRECTION

PATENT NO. : 6,224,582 B1
DATED : May 1, 2001
INVENTOR(S) : Michael K. Zachery

It is certified that error appears in the above-identified patent and that said Letters Patent is hereby corrected as shown below:

<u>Title page,</u>
Column 2, line 49, insert -- 11-- after "sheet".

Signed and Sealed this

Twentieth Day of November, 2001

Attest:

*Nicholas P. Godici*

NICHOLAS P. GODICI
*Attesting Officer*  *Acting Director of the United States Patent and Trademark Office*